United States Patent [19]
Bille et al.

[11] Patent Number: 6,155,684
[45] Date of Patent: Dec. 5, 2000

[54] METHOD AND APPARATUS FOR PRECOMPENSATING THE REFRACTIVE PROPERTIES OF THE HUMAN EYE WITH ADAPTIVE OPTICAL FEEDBACK CONTROL

[75] Inventors: Josef Bille; Frieder Loesel, both of Heidelberg, Germany

[73] Assignee: Perfect Vision Optische Geraete GmbH, Heidelberg, Germany

[21] Appl. No.: 09/334,774

[22] Filed: Jun. 16, 1999

Related U.S. Application Data

[63] Continuation-in-part of application No. 09/332,297, Jun. 11, 1999.

[51] Int. Cl.[7] .................................................. A61B 3/10
[52] U.S. Cl. ............................................................ 351/212
[58] Field of Search ................................. 351/205, 206, 351/211, 212, 214, 221; 623/4, 5

[56] References Cited

U.S. PATENT DOCUMENTS

| | | |
|---|---|---|
| 4,579,430 | 4/1986 | Bille . |
| 4,732,473 | 3/1988 | Bille et al. . |
| 4,772,115 | 9/1988 | Gersten et al. . |
| 4,838,679 | 6/1989 | Bille ........................................ 351/205 |
| 4,848,340 | 7/1989 | Bille et al. . |
| 4,887,592 | 12/1989 | Loertscher . |
| 4,988,348 | 1/1991 | Bille . |
| 5,062,702 | 11/1991 | Bille . |
| 5,777,719 | 7/1998 | Williams et al. . |

OTHER PUBLICATIONS

Liang, Junzhong et al, Objective measurement of wave aberrations of the human eye with the use of a Hartmann–Shack wave–front sensor, *J. Opt. Soc. Am A*, vol. 11, No. 7, Jul. 1994, pp. 1949–1957.

Walsh, G. et al. Objective technique for the determination of monochromatic aberrations of the human eye, *J. Opt. Soc. Am A* vol. 1, No. 9, Sep., 1984.

Wang, J. Y., et al., Wave–front interpretation with Zernike polynomials, *Applied Optics*, vol. 19, No. 9, May 1, 1980, pp. 1510–1518.

*Primary Examiner*—George Manuel
*Attorney, Agent, or Firm*—Nydegger & Associates

[57] ABSTRACT

A system for precompensating the refractive properties of an eye includes optical components for directing a beam of light through the eye for reflection from the retina. The reflected beam, which includes the refractive aberrations caused by the eye, is then separated into a plurality of individual beams by a lenslet. The plurality of individual beams are then collectively analyzed by a computer to establish an acuity map for the eye. Next, the acuity map is reversed by the computer to generate a negative acuity map, and this negative acuity map is then used to electronically configure the reflective surface of an active mirror in accordance with the negative acuity map. Subsequently, incoming light from a stimulus is reflected from the active mirror, and is thereby precompensated before reaching the eye as an undistorted light beam. It is contemplated by the present invention that a time history of the various active mirror configurations that are required by an eye can be used for diagnostic purposes.

21 Claims, 4 Drawing Sheets

METHOD AND APPARATUS FOR PRECOMPENSATING THE REFRACTIVE PROPERTIES OF THE HUMAN EYE WITH ADAPTIVE OPTICAL FEEDBACK CONTROL

This application is a continuation-in-part of application Ser. No. 09/332,297 for METHOD AND APPARATUS FOR MEASUREMENT OF THE REFRACTIVE PROPERTIES OF THE HUMAN EYE by Josef Bille and Frieder Loesel, inventors, filed Jun. 11, 1999, which is currently pending. The contents of the aforementioned Application filed Jun. 11, 1999 are incorporated herein by reference.

FIELD OF THE INVENTION

The present invention pertains generally to apparatus which have dynamically adaptive optical elements that are useful for correcting or diagnosing refractive aberrations of a human eye. More particularly, the present invention pertains to methods and devices which use adaptive optics, such as an active mirror, to precompensate for the refractive aberrations of an eye and thereby improve a person's clarity of vision. The present invention is particularly, but not exclusively, useful as a method or a device which can sequentially reconfigure an active mirror for clarity of vision, or to generate a time history of changes in the refractive properties of an eye for subsequent diagnostic purposes.

BACKGROUND OF THE INVENTION

In the perfect eye, an incoming beam of light is focused through the cornea and through the crystalline lens in a way which causes all of the light from a point source to converge at the same spot on the retina of the eye. This convergence occurs because all of the optical path lengths, for all light in the beam, are equal to each other. Stated differently, in the perfect eye, the time for all light to transit through the eye will be the same regardless of the particular path that is taken by the light.

Not all eyes, however, are perfect. The consequences of this are that light path lengths through the eye become distorted and are not all equal to each other. Thus, light from a point source that transits an imperfect eye will not necessarily be focused on the retina, or to the same spot on the retina.

As light enters and passes through an eye it is refracted at the anterior surface of the cornea, at the posterior surface of the cornea, and at the surfaces of the crystalline lens. It is after all of these refractions have occurred that the light finally reaches the retina. As indicated above, in the case of the perfect eye, all of these refractions result in no overall change in the optical path lengths of light in the incoming beam. Therefore, any deviations which result in unequal changes in these optical path lengths are indicative of imperfections in the eye which may need to be corrected.

In general, vision difficulties in the human eye can be characterized by the changes and differences in optical path lengths that occur as light transits through the eye. These difficulties are not uncommon. Indeed, nearly one half of the world's population suffers from imperfect visual perception. For example, many people are near-sighted because their eyeballs are "too long" (myopia). As a result, the sharp image of an object is generated not on the retina, but in front of or before the retina. Therefore, for a myopic person a distant scene appears to be more or less blurred. On the other hand, hyperopia is a condition wherein the error of refraction causes rays of light entering the eye parallel to the optic axis to be brought to a focus behind the retina. This happens because the eyeball is "too short" from front to back. This condition is commonly referred to as far-sightedness. Unlike the myopic person, a hyperopic, or far-sighted, person will see a near scene as being more or less blurred.

Another refractive malady is astigmatism. Astigmatism, however, is different than either myopia or hyperopia in that it results from an unequal curvature of the refractive surfaces of the eye. With astigmatism, a ray of light is not sharply focused on the retina but is spread over a more or less diffuse area. Further, there are even higher order refractive maladies of interest for vision correction which include coma and spherical aberration. More specifically, coma is an aberration in a lens or lens system whereby an off-axis point object is imaged as a small pear-shaped blob. Coma is caused when the power of the zones of the lens varies with distance of the zone from the axis. Spherical aberration, on the other hand, results from loss of definition of images that are formed by optical systems, such as an eye. Such aberrations arise from the geometry of a spherical surface.

In the past, simple refractive errors of the human eye (myopia, hyperopia and astigmatism) have been corrected conventionally with glasses, dating back to the year 1750. More recently, contact lenses, which were invented about 50 years ago, have been useful for correcting these same more simple refractive errors. Further, refractive laser surgery using Excimer UV-lasers is receiving increased popularity. Thus far, however, all of these techniques for correcting optical impairments of the eye have been limited to the correction of errors from near-sightedness (myopia) or far-sightedness (hyperopia), and to the cylindrical refractive errors, the so-called astigmatism.

As noted above, vision and its refractive errors can be quite complex. Similar to every other optical system, in addition to the simple refractive errors, the human eye also shows higher order refractive errors ("aberrations") such as coma and spherical aberration mentioned above. In all cases, aberrations result when an ideally flat 'wavefront' (i.e. a condition wherein all optical path lengths are equal) is distorted by a real-world optical system. In some cases, these distortions occur in a very complex way. In the trivial case, simple distortions like near-sightedness and far-sightedness would result in an uncomplicated bowl-like symmetrical distortion. With higher order aberrations, however, the result is a complex non-symmetrical distortion of the originally flat wavefront. It is these non-symmetrical distortions which are unique for every optical system, including every single person's eye, and which lead to blurred optical imaging of viewed scenes.

It happens that refractive errors (aberrations or distortions) are stronger when light not only passes through the center of an optical system, but also through the outer regions of the system. Specifically, these aberrations are more pronounced under critical lighting conditions (e.g., twilight). For example, it is well known that people have a comparably small pupil in bright daylight. As the light level decreases, however, the pupil becomes dilated in order to let more light pass through to the retina. With dilation, in addition to passing through the center of the eye light rays will also pass through the outer region of the eye (e.g. the optical system), where the optical quality is low. Thus, even persons with normal 20/20 vision have decreased visual acuity under critical light conditions due to increased higher order aberrations.

A typical approach for improving the vision of a patient has been to first obtain measurements of the eye which relate to the topography of the anterior surface of the cornea. Specifically, such measurements are made to determine the Zernike polynomials. The Zernike polynomials are then used to mathematically describe and to model the anterior surface of the cornea. In accordance with this practice, depending on the order of the Zernike polynomial a certain refractive condition of the eye can be described. For example, the first order terms of the Zernike polynomials describe the tilt of a wavefront while second order terms describe myopia, hyperopia and astigmatism. Third order terms then describe coma and fourth order terms describe i.e. spherical aberration.

Until now, the complex aberrations of the human eye involving coma and spherical aberration could not be measured and, therefore, they could not be corrected. Further, even today, the measurement of the 'standard' so-called simple refractive errors is still not fully objective. In fact, presently the patient's vision is usually categorized using an autorefractor for measuring near-sightedness, farsightedness, and astigmatism. In the process, cooperation of the patient is crucial for obtaining even rough realistic results with these systems. Still, after this rough initial measurement, the optometrist has to use correction lenses in a subjective procedure to find the corrective strength that is best suited for the patient. To a great extent, these limitations have been caused by an inability to determine a topography for the posterior surface of the eye in addition to determining the topography of the anterior surface. Further, there has been little attention given to the peripheral areas of the cornea where spherical aberrations become more prominent as the pupil of the eye dilates. In order to overcome these deficiencies, it is necessary to evaluate new ways and methods for measuring the refractive characteristics of the cornea.

Heretofore, it has been a common practice to analyze and describe light beams in terms of wavefronts and aberrations of a wavefront. In this regard, the Zernike polynomials have been helpful. A light beam, however, can be conceptualized in a different way; other than as a wavefront. It can also be thought of in terms of a plurality of individual beams, each of which has its own optical path length. Specifically, by way of comparison, at any particular point in time a wavefront can be thought of as being the temporal lengths of the various optical paths that have been traveled by individual light beams from the origin or source of the light. Thus, a light beam with a flat or planar wavefront is equivalent to a light beam wherein all light in the beam has traveled on optical paths that have the same temporal length. A wavefront can be distorted by imperfections in the eye and result in so-called wave aberrations. In terms of optical path lengths, these same aberrations can be thought of as resulting from differences in the optical path lengths of individual beams which are caused by undesirable refractions of light as it passes through the eye.

As discussed above, until now vision correction has been primarily concerned with reshaping the cornea using data that is collected about the topography of the anterior surface of the eye. A good example of technology that is useful for this purpose is provided in U.S. Pat. No. 5,062,702 which issued to Bille for an invention entitled "Device for Mapping Corneal Topography." The posterior surface of the eye, however, also affects the refraction of light as it passes through the eye. Thus, additional information about the thickness of the cornea is necessary for more precise refractive corrections. To this end, a map of the posterior surface of the cornea would undoubtedly be useful. Further, while gross approximations of the lower order visual aberrations using the Zernike polynomials may be useful for limited purposes, the superficial models provided by the Zernike polynomials become quite cumbersome and less precise when higher order aberrations are concerned.

In light of the above, it is an object of the present invention to provide a method and apparatus which use adaptive optics that will precompensate for the refractive aberrations of a human eye. Another object of the present invention is to provide a method and apparatus which can sequentially reconfigure an active mirror to generate a time history of changes in the refractive properties of an eye for subsequent diagnostic purposes. Yet another object of the present invention is to provide a method and apparatus for measuring the refractive properties of the human eye which, in addition to myopia, hyperopia and astigmatism, can also be used to determine higher order refractive error (aberrations) such as coma and spherical aberration. Still another object of the present invention is to provide a method and apparatus for measuring and precompensating for the refractive properties of the human eye which are effectively easy to use, relatively simple to operate and implement, and comparatively cost effective.

SUMMARY OF THE PREFERRED EMBODIMENTS

In accordance with the present invention, a system and method for precompensating the refractive properties of an eye include optical components for selectively generating a beam of collimated light. For the present invention, this beam of collimated light is directed through the eye for reflection from the retina. A lenslet array is then used to separate the light in the reflected beam into a plurality of individual beams which will each have a unique optical path length. Specifically, each optical path length will be indicative of the refraction that was experienced by its respective individual beam during transit of the individual beam through the eye. Next, the optical path lengths of the individual beams are collectively used by a computer to create a digitized acuity map of the eye.

Once the digitized acuity map has been created, it is electronically reversed in the computer to generate a signal which, in effect, is a negative acuity map. This signal is then sent to an active mirror and used for programming the individual facets (pixels) of the active mirror to recreate a negative of the acuity map. Subsequently, incoming light from a stimulus is reflected by the preprogrammed active mirror.

As intended for the present invention, the reflection of an incoming beam from the preprogrammed active mirror will make the optical path lengths of individual beams in any incoming beam appear to be substantially equal to each other. In this way, an incoming beam from a stimulus is precompensated to account for the refractive aberrations of the eye that are evidenced by the acuity map.

Several alternative embodiments for the system of the present invention are contemplated. For one, the system can include a variable aperture for controlling the size of the collimated light beam as it is directed toward the eye for reflection from the retina. If used, the variable aperture should be moveable between a first configuration wherein the light beam has a diameter of approximately 2 mm as it passes through the pupil toward the retina, and a second configuration wherein the light beam has a diameter of approximately 6 mm as it passes through the pupil toward the retina. In both cases, the light that is reflected from the retina will fill the pupil as it leaves the eye. Thus, for each configuration of the variable aperture, an acuity map can be created which, for convenience, are hereinafter referred to respectively as a first acuity map and a second acuity map.

For another embodiment of the present invention, the system can further include optical components for creating a topographical map of the anterior surface of the cornea. For this embodiment, a light beam is generated and focused for reflection from the anterior surface of the cornea. Again, as was done with light reflected from the retina, a lenslet array is used to separate the light beam that is reflected from the cornea into a plurality of individual beams. Again, each individual beam has a unique optical path length. In this case, however, the optical path lengths are indicative of the shape of the anterior surface of the cornea and, accordingly, are used in the computer to create the topographical map of this surface.

For diagnostic uses of the present invention, the topographical map of the cornea is indicative of aberrations that are caused by the anterior surface of the cornea. Similarly, the first acuity map and the second acuity map are indicative of aberrations for the entire eye. Thus, these maps, and a predetermined value for the relaxed state refraction of the eye's crystalline lens, can all be used together to determine the topography of the posterior surface of the cornea. Specifically, a comparator which is operable with the computer can be used to separate the aberrations of the anterior surface of the cornea (topographical map), and the predetermined aberration for the lens, from the aberrations of the entire eye (first and second acuity maps). The result can then be used to determine aberrations for the posterior surface of the cornea which are useful for modeling this surface.

As an additional diagnostic tool, the system of the present invention can be activated to obtain a plurality of successive measurements. By using the plurality of signals that are generated from these measurements, a time history of the refractive properties of the eye can be made. The computer can then use this time history for diagnosing pathological problems of the eye.

It is also contemplated that the system of the present invention can be used to control the spatially distributed ablation pattern of an excimer laser. Specifically, by using the plurality of surface positions of the individual facets of the active mirror, a direct template of the target surface shape of the cornea can be obtained. A computer can then use this template to control the amount of ablation that is to be accomplished by the excimer laser within a particular target spatial area. During the procedure that is being performed by the excimer laser, the resulting spatially modulated surface profile can be measured by the adaptive optical closed-loop system of the present invention. This can be done in an iterative measurement process. Accordingly, a measure of quality assurance can be immediately provided after the completion of the laser ablation procedure.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
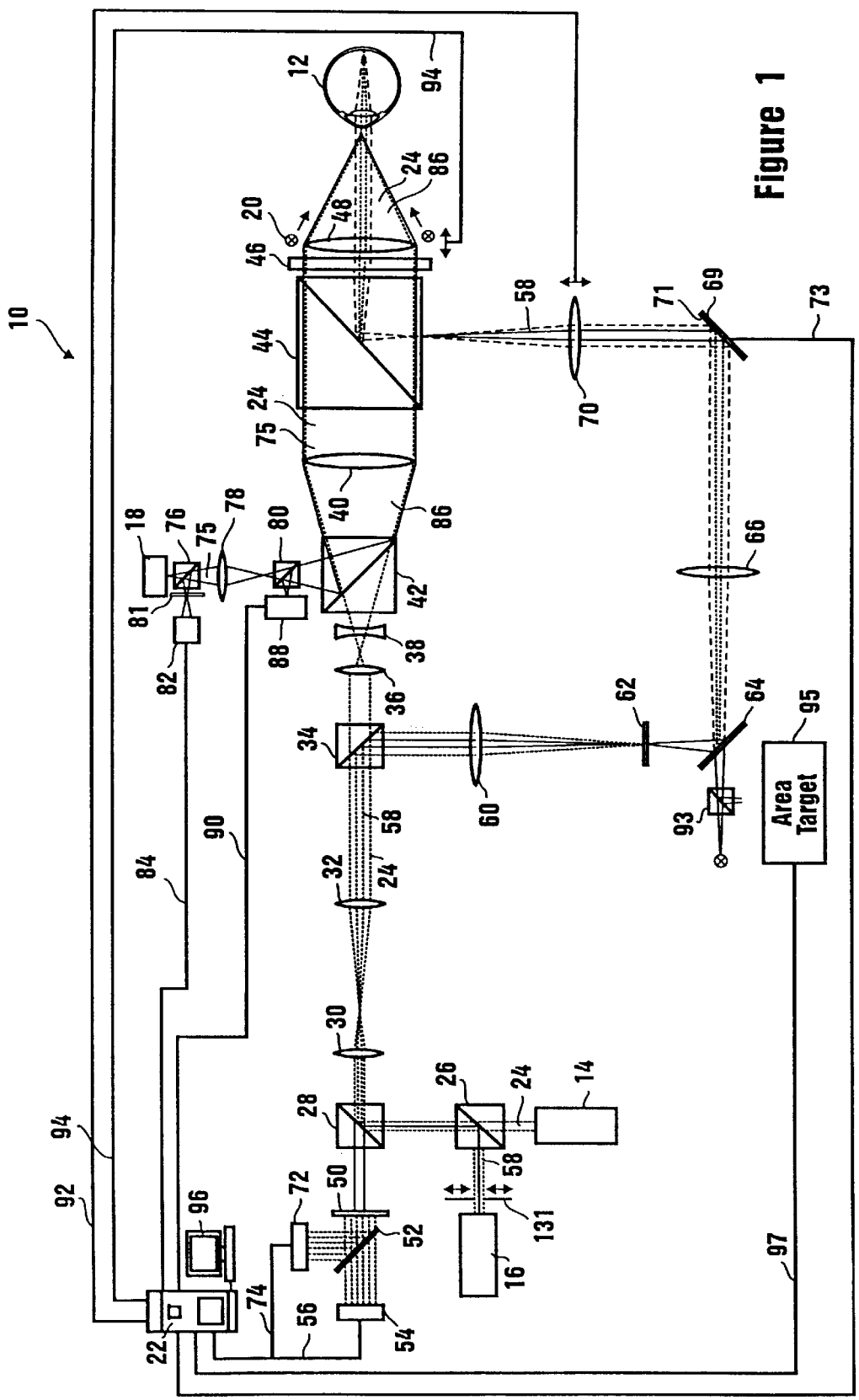
FIG. 1 is a schematic drawing of the system of the present invention.

Referring initially to FIG. 1, a system for determining the refractive properties of the human eye is shown in a schematic drawing and is generally designated 10. As impliedly indicated in FIG. 1, use of the system 10 is intended to provide diagnostic information about the eye 12. In order to do this, the system 10 employs four different light sources and uses four different wavelengths, all for different purposes. More specifically, the system 10 includes a light source 14 which is preferably a laser diode that generates a light beam having a wavelength of approximately eight hundred and forty nanometers (840 nm). Another light source 16 is provided which is preferably a laser diode that will generate a light beam having a wavelength of approximately seven hundred and eighty nanometers (780 nm). There is still another light source 18 which is preferably a laser diode that will generate a light beam having a wavelength of approximately nine hundred and thirty nanometers (930 nm). Finally, there is an illuminator 20 which can include a plurality of infrared diodes that will collectively generate a light beam having a wavelength of approximately nine hundred and eighty nanometers (980).

As intended for the system 10 of the present invention, a computer 22 is used to evaluate the light that is emitted from each of the above mentioned light sources 14, 16 and 18, and from the illuminator 20. More specifically, this evaluation is conducted by the computer 22 after the light from its respective source has been directed toward, and reflected in some way from the eye 12. With the objective of considering the collective effect of all light that is reflected in the system 10 from the eye 12, it is perhaps best to first consider each source of light individually, and to track light from that particular source as it passes through the system 10.

Beginning at the light source 14, as stated above, a light beam 24 having a wavelength of approximately eight hundred and forty nanometers (840 nm) is generated. Further, the light source 14 directs this beam 24 toward a dichroic beam splitter 26 which will pass 840 nm light, but which will otherwise reflect light that is substantially below 840 nm (e.g. 780 nm). After passing through the beam splitter 26, the light beam 24 is then reflected by a polarizing beam splitter 28 for further transmission by a beam expander that includes the lenses 30 and 32. The light beam 24 then passes through a dichroic beam splitter 34 which, like the beam splitter 26, will pass 840 nm light but reflect 780 nm light. After passing through the beam splitter 34, the light beam 24 is expanded by the collective effect of lenses 36, 38 and 40, and it passes through the dichroic beam splitter 42 toward the dichroic beam splitter 44. For purposes of the present invention, the dichroic beam splitter 42 will pass light having wavelengths below about 900 nm and will reflect light having wavelengths above about 900 nm. On the other hand, the dichroic beam splitter 44 will pass light having wavelengths above about 830 nm and will reflect light having wavelengths below about 830 nm. Thus, the light beam 24 will pass through both of the beam splitters 42 and 44. Upon passing through the beam splitter 44, the light in light beam 24 passes through a quarter wave plate 46 where it is rotated about forty five degrees (45°). The light beam 24 is then focused by a moveable lens 48 onto the eye 12.

In reflection from the eye 12, the light beam 24 passes back through the quarter wave plate 46 where it is again rotated an additional forty five degrees (45°). Thus, it is now rotated about ninety degrees (90°) relative to the light in light beam 24 as it was being initially emitted from light source 14. Further, the reflected light beam 24 passes back through the beam splitters 10 44, 42, and 34. Due to its dual rotation by the quarter wave plate 46, however, light beam 24 will not be reflected by the polarizing beam splitter 28. Instead, the polarizing beam splitter 28 will pass the light beam 24 toward a lenslet array 50 where the beam 24 is separated into a plurality of individual beams. These individual beams are all mutually parallel, and from the lenslet array 50 they are directed toward a dichroic beam splitter 52 which, like beam splitters 26 and 34, will pass light having a wavelength of 840 nm. After passing through the beam splitter 52, the individual beams which now comprise the beam 24 are received by an area sensitive detector 54 and are then passed as a plurality of respective signals via the line 56 to the computer 22. Preferably, the area sensitive detector 54 is a CCD of a type well known in the pertinent art.

In a manner similar to that set forth above for describing the path taken by light beam 24, consider now the light beam 58 that is generated by the light source 16. As indicated above, the light beam 58 will have a wavelength that is about 780 nm. Therefore, the light beam 58 will be reflected by the dichroic beam splitter 26 and the polarizing beam splitter 28. Unlike the light beam 24, however, the light beam 58 will be reflected by the beam splitter 34 and directed toward the lens 60 and pinhole 62. A dichroic beam splitter 64 is then provided to direct the light beam 58 through a lens 66, toward an active mirror 69. It can be noted that for purposes of the present invention, the beam splitter 64 needs to be able to pass visible light below a wavelength of 780 nm (i.e. light in the wavelength range of 780–380 nm).

For the purposes of system 10, the active mirror 69 can be of any type well known in the pertinent art which has a reflective surface 71 that is electronically alterable. Preferably, the reflective surface 71 of active mirror 69 has a plethora of individual facets or pixels which are each separately responsive to a dedicated electronic signal that can be passed via the line 73 from the computer 22 to the active mirror 69.

After being reflected from the reflective surface 71 of active mirror 69, the light beam 58 will be directed through a focusing lens 70 toward beam splitter 44. After being reflected by the beam splitter 44, the light beam 58 is rotated by quarter wave plate 46 and directed by focusing mirror 48 toward the eye 12. Importantly, as light beam 58 is directed toward the eye 12, the light in light beam 58 will be substantially collimated and have a beam diameter that is approximately in a range between two and six millimeters (2–6 mm).

When reflected from the eye 12, the light beam 58 will again be rotated by the quarter wave plate 46. Thus, it will be reflected by the beam splitter 44, turned by active mirror 69 and reflected by the beam splitters 64 and 34. Like the light beam 24, light beam 58 will be passed by the polarizing beam splitter 28 toward the lenslet array 50. Also like the light beam 24, the light beam 58 will be separated into a plurality of individual light beams by the lenslet array 50. The plurality of individual light beams which now comprise the light beam 58 are reflected by the beam splitter 52 and are directed toward an area sensitive detector 72 where the individual beams are converted into respective signals for further transmission via line 74 to the computer 22.

The light source 18, as mentioned above, will generate a light beam 75 which has a wavelength of approximately 930 nm. As shown in FIG. 1, this light beam 75 will pass through a polarizing beam splitter 76, a lens 78 and a dichroic beam splitter 80, before being reflected toward the eye 12 by the beam splitter 42. Importantly, as the beam 75 is directed toward the eye 12 it will pass through and be rotated by the quarter wave plate 46. The light beam 75 is then reflected from the eye 12, and light in the reflected light beam 75 will again pass through, and be rotated by, the quarter wave plate 46. At the 12 beam splitter 42, the light beam 75 will be directed back toward the polarizing beam splitter 76. This time, however, light beam 75 does not pass through the beam splitter 76. Instead, due to its rotations by the quarter wave plate 46, the light beam 75 is reflected by the polarizing beam splitter 76 through a pinhole 81 toward the confocal detector 82. A signal that is generated by the confocal detector 82 in response to its reception of the light beam 75 is then passed via line 84 to the computer 22.

As indicated above, the illuminator 20 generates a light beam 86 which has a wavelength of about 980 nm. For the present invention, the illuminator 20 can include either a plurality of separate infrared diodes, or it can be configured as a ring. In either case, as shown in FIG. 1, the resultant light beam 86 is pointed directly at the eye 12. Upon reflection of the light beam 86 from the eye 12, FIG. 1 indicates that the beam passes through the beam splitter 44 but is reflected by both the beam splitter 42 and the beam splitter 80. Specifically, insofar as the beam splitter 80 is concerned, it will reflect light such as the light in light beam 86 which has a wavelength greater than about 950 nm. Accordingly, the light in light beam 86 which has been reflected from the eye 12 will be received by a pupil camera 88 and a responsive signal generated by the pupil camera 88 will be sent via line 90 to the computer 22.

FIG. 1 also shows that the computer 22 is connected via a line 92 with the lens 70. With this connection the computer 22 is able to adjust the focus of light beam 58 that is provided by lens 70. Further, FIG. 1 shows that the computer 22 is connected via a line 94 with the lens 48. With this connection the computer 22 is able to adjust the focus of light beams 24 and 75. Also, FIG. 1 shows that the computer 22 can include a frame grabber 96 which will provide visual displays of the signals that are received from the area sensitive detectors 54 and 72, as well as the signals that are received from the confocal detector 82 and the pupil camera 88.

Still referring to FIG. 1 it will be seen that the system 10 includes an additional dichroic beam splitter 93 which is positioned between an area target 95 and the dichroic beam splitter 64. This beam splitter 93 is also positioned between a point 124 and the beam splitter 64. Thus, light from either the area target 95 or from the point 124 can be directed through the beam splitter 64 and through the system 10 toward the eye 12. Further, the area target 95 can be connected with the computer 22 via line 97 so that the particular display provided by the area target 95, and the wavelengths of light used for this display can be selectively controlled by the operator of the system 10.

OPERATION

Figure 2A:
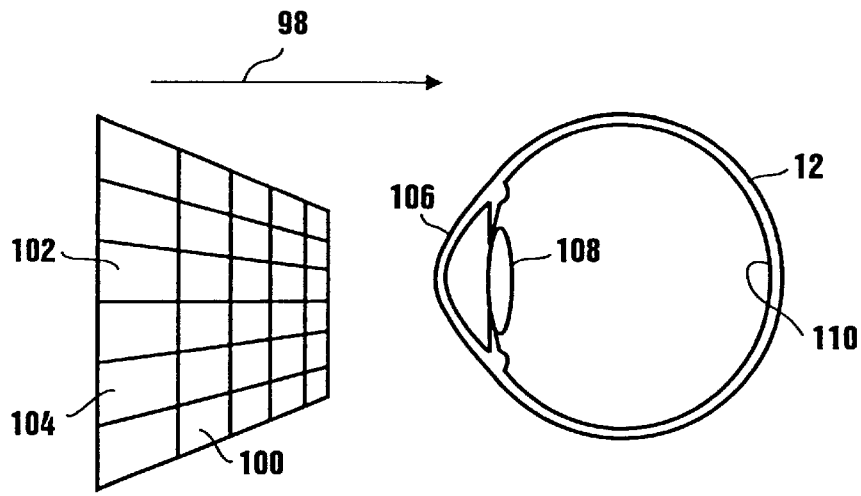
FIG. 2A is a side cross sectional view of an eye shown in relationship with an incoming planar wavefront of light.

In overview, for the purposes of the operation of system 10, light can be conceptualized in either of two ways. Firstly, light can be thought of in terms of wavefronts. Secondly, light can be thought of as being a collective bundle of many different individually separate beams. These two concepts, of course, must be related to each other if they are to describe the same light beam. Accordingly, in order to reconcile one concept with the other, a wavefront can be thought of as being a spatial representation of the optical path lengths that have been traveled from a common origin (light source) by all of the different individual beams, at any given point in time. Thus, it is the case with unrefracted light which has traveled from a light source in the direction of arrow 98, as shown in FIG. 2A, that the light will exhibit a planar wavefront 100. Stated differently, the optical path length of an individual beam in this light that has traveled from the source to a position 102 in the wavefront 100 will have the same length as the optical path length of an individual beam that has traveled from the source to a position 104 in the wavefront 100. As the light in wavefront 100 passes through the eye 12, however, the individual light beams will be refracted differently.

Figure 2B:
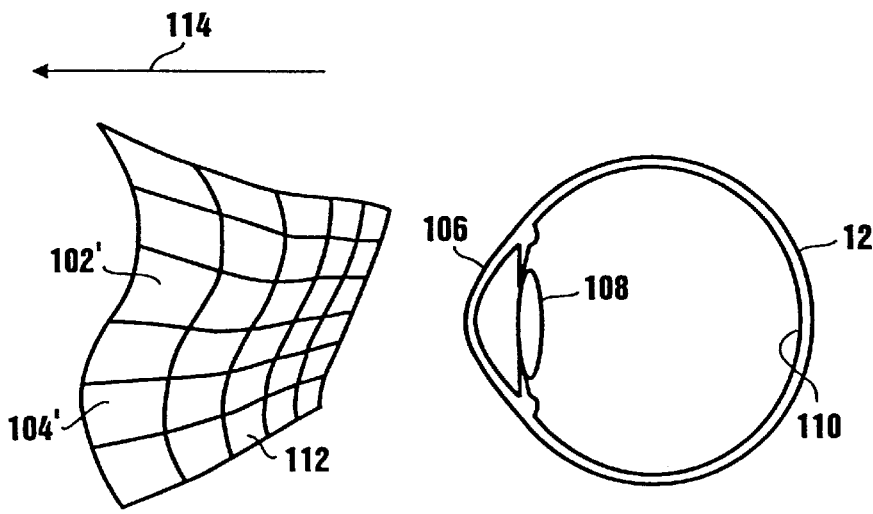
FIG. 2B is a side cross sectional view of an eye shown in relationship with an outgoing wavefront of light that has been distorted by the refractive properties of the eye.

Anatomically, it is necessary for light entering the eye 12 to pass through the cornea 106 and the crystalline lens 108 of the eye 12 before coming into contact with the retina 110. It is known that our visual perception is dependent on how this light comes into contact with the retina 110 and, it is known, of course, that in accordance with Snell's law this light will be refracted by the cornea 106 and the lens 108 as it passes into the eye 12. Further, whatever light there is that is reflected from the retina 110 to pass back through the eye 12 and away from the eye 12 will also be refracted by the lens 108 and the cornea 106. The result of all this refraction may likely be a distorted wavefront 112 which is traveling away from the eye 12 in the direction of arrow 114, such as shown in FIG. 2B. By comparing FIG. 2A with FIG. 2B it will be noted that, due to refractions caused by the eye 12, the optical path length of the individual beam which has traveled from position 102 in the planar wavefront 100 to the position 102' in the distorted wavefront 112 will be different from the optical path length of the individual beam which has traveled from position 104 to position 104'. As appreciated by the present invention, the differences in these optical path lengths is indicative of the respective refractions that were experienced by the individual beams as they transited the eye 12.

In the operation of the system 10 of the present invention, it may first be necessary to calibrate the system 10. This can be done by replacing the eye 12 with a flat mirror (not shown) and by programming the active mirror 69 to act as a flat mirror. Light can then be sequentially passed through the system 10 from the light sources 14, 16 and 18 and from the illuminator 20 for reflection back through the system 10 from the flat mirror. In this way, signals can be generated from the area sensitive detectors 54 and 72, from the confocal detector 82 and from the pupil camera 88. The signals which are thus generated will be indicative of inherent optical aberrations in the system 10 and can subsequently be used to compensate actual signals generated by the eye 12.

Once the system 10 has been calibrated, it is desirable to determine an exact spatial position for the eye 12 in x-y-z. This is done by using the confocal detector 82 and the pupil camera 88. Specifically, in order to establish a "z" position for the eye 12, the light source 18 is activated to generate the light beam 75. For the present invention, the light beam 75 is focused by the lens 48 to obtain a specular reflection of the light beam 75 from the apex 114 of the cornea 106 (see FIG. 3). Depending on the position of the lens 48, which is sensed by the computer 22, when this specular reflection is obtained the position of the eye 12, and more specifically the position of the apex 114 of eye 12, in a "z" direction along the visual axis of the eye 12 is established. In order to establish an "x-y" position for the eye 12, the illuminator 20 needs to be activated. Specifically, using intensity differences in the reflection of light beam 86 from the eye 12, as sensed by the pupil camera 88 and ultimately by the computer 22, the "x-y" position of the eye 12 is established. For the present invention, the intensity differences used for this measurement are cause by the contrast between the iris 116 and the lens 108 at the periphery of the pupil 118. While the "z" position has been considered as having been taken first in this discussion, it will be appreciated by the skilled artisan that the "x-y" determination may, in fact, be made first.

Once the system 10 is calibrated and the position of the eye 12 in "x-y" and "z" has been established, refractive measurements of the eye can be made. In light of the above discussion, it will be noted that these measurements need to be considered with knowledge of the length of the eye 12, and with an understanding that the crystalline lens 108 is in its basic relaxed state of refraction. Insofar as a measurement for the length of the eye 12 is concerned, this can be done by activating the light source 114 while the eye 12 is focused to a point 124 at infinity (see FIG. 1). The focusing lens 70 is then moved as required by the computer 22, or manually by the operator of system 10, until the light beam 24 from light source 114 is focused onto the retina 110. By using the position of the lens 70 for this focal condition, the computer 22 is able to establish a position of the retina 110. Then, by knowing the position of the retina 110, and by knowing the location of the apex 114 that was obtained from earlier measurements of the "z" position of the eye 12, the length of the eye 12 can be determined. This measurement, of course, will also determine whether the eye 12 is myopic or hyperopic.

Figure 3:
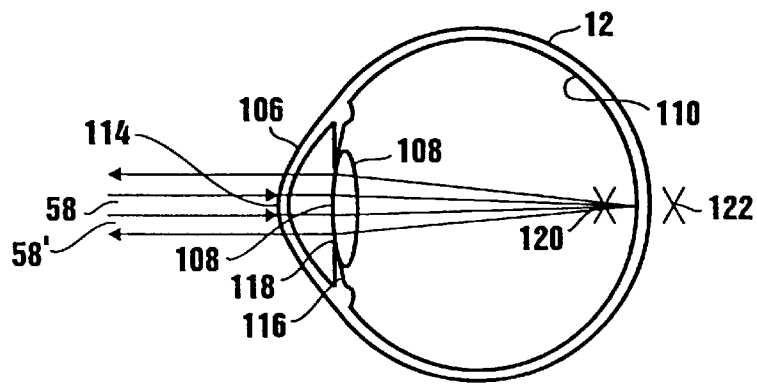
FIG. 3 is a side cross sectional view of an eye shown with light reflecting from the retina.

Referring to FIG. 3, it will be appreciated that if the light beam 24 is focused by the eye 12, without any correction, to a location 120 in front of the retina 110, and movement of the lens 70 is necessary to move the focal point of light beam 24 from the location 120 backward toward the retina 110, the eye 12 is myopic. On the other hand, if the light beam 24 is focused by the eye to a location 122 behind the retina 110, again without any correction, and movement of the lens 70 is necessary to move the focal point of light beam 24 from the location 122 forward toward the retina 110, the eye 12 is hyperopic. The determination of whether the eye 12 is myopic or hyperopic is important, not only in its own right, but also for subsequent refractive measurements. Importantly, while the myopic eye 12 focuses on the point 124 at infinity, it can be taken that the crystalline lens 70 will be in its basic relaxed state of refraction. On the other hand, as mentioned above and as explained in more detail below, when the eye 12 is hyperopic of is the eye of an infant several successive measurements need to be taken.

Figure 4:
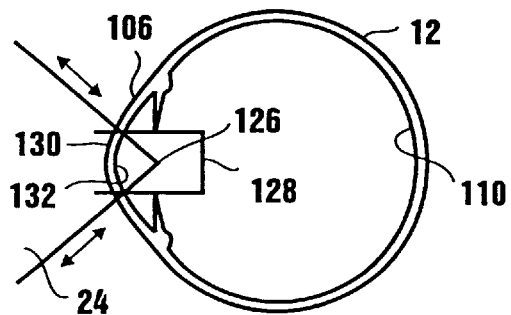
FIG. 4 is a side cross sectional view of an eye shown with light reflecting from the anterior surface of the cornea.

The initial measurement for the general topography of the cornea 106 of the eye 12 is made using the light beam 24 that is generated by light source 14, and which has a wavelength of 840 nm. By cross referencing FIG. 1 with FIG. 4 it will be seen that the light beam 24 is focused by the lens 48 toward the center of curvature 126 of the cornea 106. In doing this, the light beam 24 covers a distance 128 on the anterior surface 130 of the cornea 106 that is equal to about seven millimeters (7 mm). Importantly, some of the light in the light beam 24 will be reflected by the anterior surface 130 of the cornea 106 and will be directed back through the system 10 to the lenslet 50 where it is separated into a plurality of individual beams. These individual beams in the reflected light of light beam 24 are then detected by the area sensitive detector 54 which generates signals that are sent via line 56 to the computer 22. Using these particular signals, the computer 22 is able to create a topography map of the anterior surface 130 of the cornea 106.

For the present invention, refractive measurements of the entire eye 12 are made using the light beam 58 that is generated by light source 16. The shorter wavelength of 780 nm is selected for the light beam 58 because it is near the visible range and it will, therefore, more easily travel through the eye 12 than will the longer wavelength light beams used for other purposes in the system 10. It is an important consideration that the light beam 58 have a relatively small cross section as it initially enters the eye 12. This is so in order to minimize light refractions that are caused as the light beam 58 travels through the eye 12 toward the retina 110. For the present invention, the light beam 58 is, preferably, initially confined to about two millimeters (2 mm) diameter. As implied above, however, a variable aperture 131 may be incorporated with the light source so that the diameter of the light beam 58 can be selectively varied from about two millimeters to about six millimeters (2–6 mm). As discussed in more detail below, the variable aperture 131 is provided so that different refractive measurements can be made of the eye 12 from essentially the same perspective. Also, the light beam 58 is adjusted by the optics along its beam path so that as the light beam 58 leaves the lens 48 and travels toward the eye 12, it is substantially collimated when it arrives at the anterior surface 130 of the cornea 106.

Returning to FIG. 3, it will be seen that the light in light beam 58 will be reflected from the retina 110 as a light beam 58' which fills the pupil 118. This reflected light beam 58' then is passed back through the system 10 to the lenslet 50 where, like the beam 24, it is separated into a plurality of individual beams. Also like the individual beams of light beam 24, the individual beams of light beam 58 are passed to an area sensitive detector 72 where signals are generated for transmission via line 74 to the computer 22. More specifically, the individual beams of light beam 58 are collectively used to generate an acuity map of the eye 12 which is indicative of the refractions experienced by light as it passes through the eye 12. In accordance with the present invention, and for purposes of distinguishing the measurements taken by system 10, whenever the variable aperture 131 at light source 16 is set to provide a 2 mm diameter for the light beam 58, the resultant acuity map will be referred to herein as a first acuity map. On the other hand, whenever the variable aperture 131 is set to provide a wider 6 mm diameter for the light beam 58, the resultant acuity map will be referred to herein as a second acuity map.

For a myopic eye 12, which will remain in its basic relaxed state of refraction while focused to infinity on the point 124 (see FIG. 1), a topography for the posterior surface 132 of the cornea 106 can be determined using computer 22. Basically, this is done by subtracting the topography map data for the anterior surface 130 of the eye 12, and the basic relaxed state refraction for the crystalline lens 108, from the acuity map of the entire eye 12. The result is data which can be used directly to determine the topography for the posterior surface 132 of the eye 12.

Figure 5:
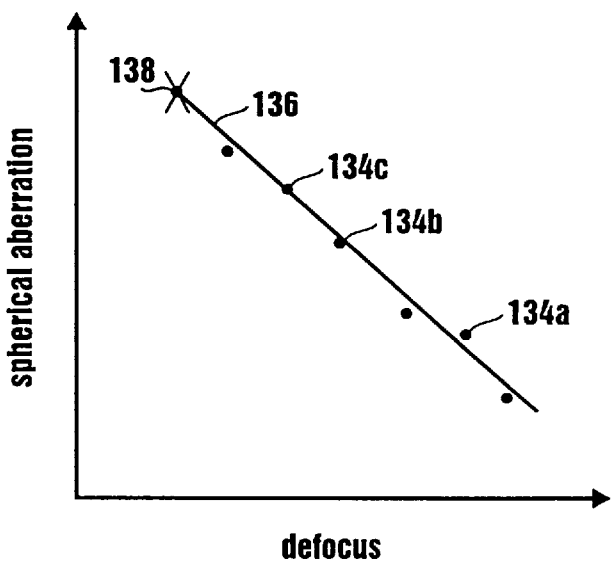
FIG. 5 is a graph showing the relationship between defocus conditions of an eye and the spherical aberration exhibited by the lens of the eye in a respective defocused condition.

For a hyperopic eye 12 or an infant eye 12, which is not able to establish its basic relaxed state of refraction while focused to infinity on the point 124, successive measurements need to be taken and the collected data extrapolated to determine the basic relaxed state of refraction. This is possible because it is known that there is a generally linear relationship between each defocus condition of the crystalline lens 108 in the eye 12, and the corresponding spherical aberrations caused by the lens 108 (see FIG. 5). Therefore, by taking a series of successive measurements for the acuity map (i.e. using the light beam 58 from light sources 16) a plurality of data points 134 (of which the data points 134a, 134b and 134c are representative), can be plotted. In FIG. 5 it is seen that the plots of data points 134 can be used to identify a line 136 and that the point 138 can be extrapolated and be considered equivalent to the conditions extant when the crystalline lens 108 is in its basic relaxed state of refraction. In a manner as disclosed above in consideration of the myopic eye 12, this data can be used with the topography map of the anterior surface 130 of the cornea 106 and the acuity map of the entire eye 12 to determine a topography map for the posterior surface 132 of the eye 12. In any case, all of the data collected will give the operating physician a much more detailed measurement of the anatomy of the eye 12 which will be useful for the prescription of corrective elements or for planning the conduct of refractive surgery.

As a diagnostic tool the system 10 shown in FIG. 1 is also useful for creating an enhanced acuity map and for determining a time history of the refractive properties of the eye 12. Both of these abilities are, of course, beneficial to the operator of the system 10.

Insofar as an enhanced acuity map is concerned, such a map can be made by operation of the variable aperture 131 that functions in conjunction with the light source 16. More specifically, with the variable aperture 131 set to provide a 2 mm diameter light beam 58 at the point where the light beam 58 enters the eye 12, there will be minimal refraction of the light beam 58 as it passes through the cornea 106 and the lens 108 toward the retina 110. Upon reflection of the light beam 58 from the retina 110, however, the light beam 58 will fill the pupil 118 as it passes back out of the eye 12. The result is a reflected light beam 58 that is basically refracted by the lens 108 and the cornea 106 during only one pass of the light beam 58 through the eye 12. The acuity map which is made from this beam has been referred to above as a first acuity map. On the other hand, with the variable aperture 131 enlarged to provide a 6 mm diameter light beam 58 at the point where the light beam 58 enters the eye 12, there will be refraction of the light beam 58 by the cornea 106 and the lens 108 during two passes of the light beam 58 through the eye 12. First, light beam 58 will be refracted as it passes into the eye 12 toward the retina 110. Second, the light beam 58 will be refracted again, as the light beam 58 is reflected from the retina 110 and out of the eye 12. The acuity map which is made from this beam 58 has been referred to as the second acuity map.

Once the first and second acuity maps have been generated, they can be compared and reconciled by the computer 22 to provide an enhanced acuity map. This enhanced acuity map can, of course, be used in the manner described above to determine a topography for the posterior surface 132 of the cornea 106.

An additional aspect of the system 10 is that it can be dynamically operated to obtain a time history of the refractive properties of the eye. This is possible because of the active mirror 69. Specifically, each time a topography map is made of the anterior surface 130 of the eye 12 with the light beam 24, and an acuity map is made of the entire eye 12 with the light beam 58, the collective effect of these maps are used to establish a configuration for the reflective surface 71 of the active mirror 69. New configurations for the reflective surface 71 of the active mirror 69, however, can be successively made in very short order. A collection of these configurations, which can be recorded by the computer 22, will serve as a time history of the refractive properties of the eye 12 and can be used by the physician for diagnosis.

AN ALTERNATE EMBODIMENT

Figure 6:
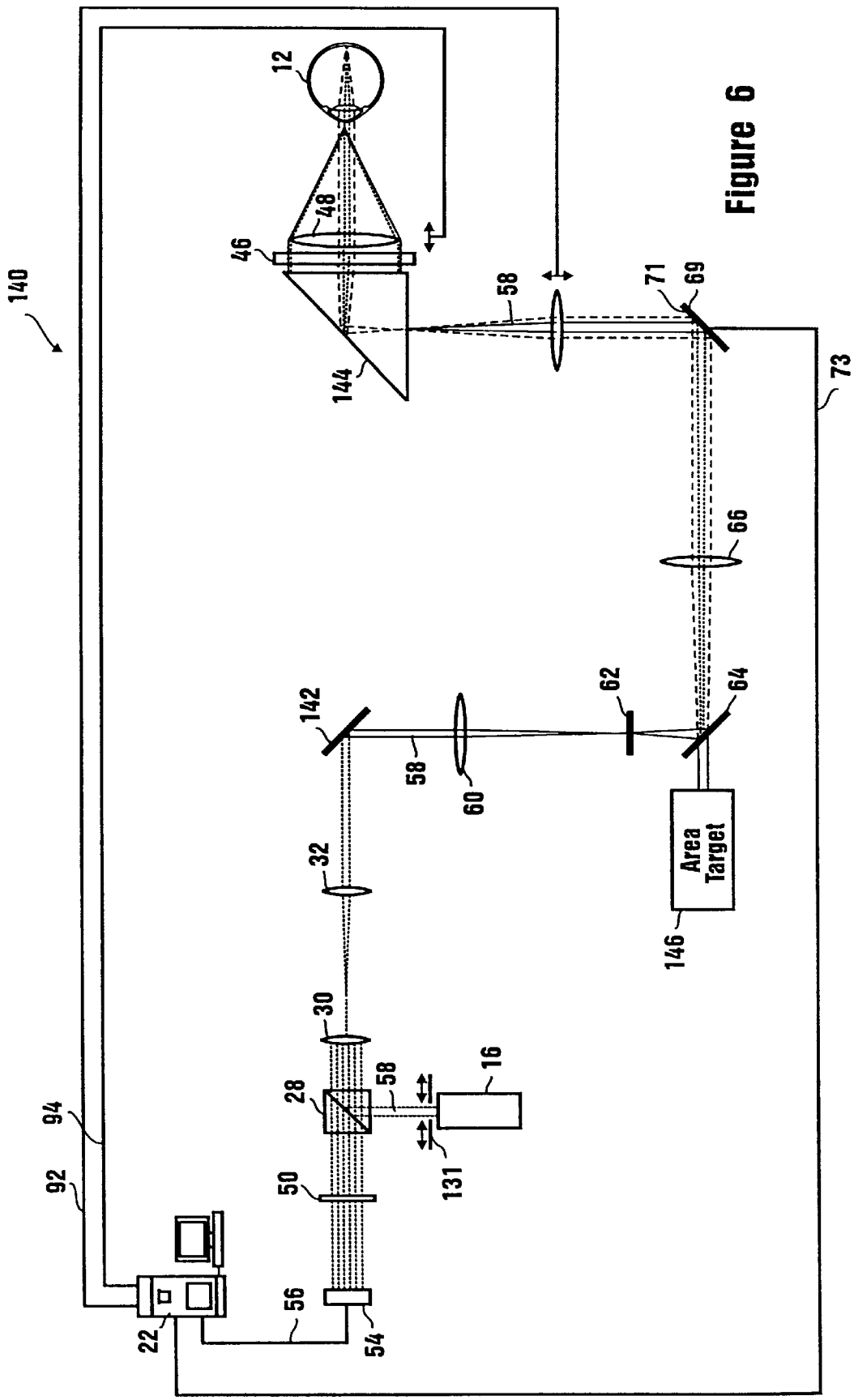
FIG. 6 is a schematic drawing of an alternate embodiment for the system of the present invention.

Referring now to FIG. 6, an alternate embodiment of the present invention is shown and is generally designated 140. Unlike the system 10 described above, which is primarily useful for diagnostic purposes, the system 140 shown in FIG. 6 is more suited to routine, recreational and avocational activities where corrective optics are necessary or desirable for clarity and sharpness of vision. Accordingly, many of the subassemblies and components that are necessary for the diagnostics operation of the system 10 can be eliminated from the practical applications of the system 140. Specifically, the optical components that were necessary for precisely determining a position for the eye 12 in the system 10 are not needed for the system 140. These components include the light source 18, the illuminator 20, the confocal detector 82 and the pupil camera 88. Further, the light source 14 can also be eliminated. Consequently, the dichroic beam splitters 34 and 44 in system 10 can be respectively replaced with turning mirrors 142 and 144 in the system 140. Otherwise, the components which are common to both the system 10 and the system 140, and which function in the same way, are given the same numerical designation as provided above for the system 10.

In overview, the system 140 relies on an acuity map that is generated by analyzing the light beam 58 from light source 16 in a manner similar to that described above for the system 10. The digitized acuity map that is thereby generated from individual beams in the reflected light beam 58 is then reversed by the computer 22. This, in effect, creates a negative acuity map that is also digitized. This negative acuity map is then sent as a signal via line 73 to the active mirror 69 where it is used to configure the reflective surface 71 of the active mirror 69. With the reflective surface 71 configured by the negative acuity map, incoming light from a stimulus, such as an area target 146, will be precompensated to account for the refractive aberrations of the eye 12. This, of course, is done before the light from the stimulus (area target 146) is received at the eye 12. As intended for the present invention, a negative acuity map can thus be produced as frequently as necessary or desired by the operator.

Figure 7:
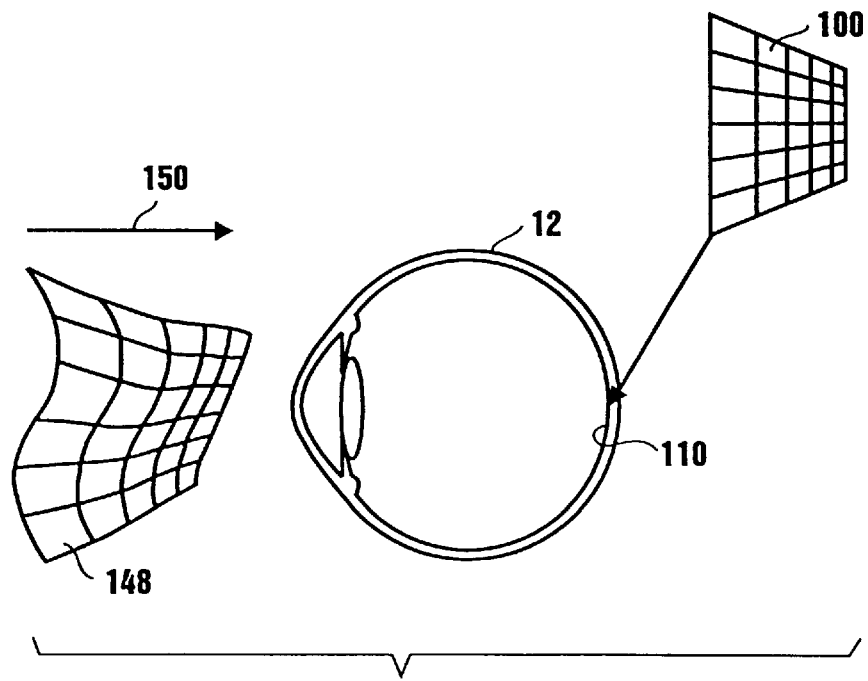
FIG. 7 is a side cross sectional view of an eye shown receiving a precompensated wavefront.

A general appreciation for the optical machinations which result from the systems 10 (FIG. 1) and 140 (FIG. 6) of the present invention will be gained by reference to FIG. 7. When referring to FIG. 7, however, it is to be understood that the active mirror 69 has already been preprogrammed with a negative acuity map in a manner as disclosed above. Consequently, unaltered light coming directly from the area target 146 will be altered by the active mirror 69. Specifically, as this light is reflected by the active mirror 69 it will be converted from a planar wavefront 100 into a precompensated wavefront 148. As intended for the present invention, this precompensated wavefront 148 will, in effect, be a remodel of the negative acuity map that is programmed into the active mirror 69. It is this precompensated wavefront 148 which then continues through the system 140 in the direction of arrow 150 toward the eye 12. As the precompensated wavefront 148 passes through the eye 12. It then happens that the refractive characteristics of the eye 12 change the precompensated wavefront 148 in a manner such that the perception at the retina 110 of eye 12 is a corrected planar wavefront 100.

While the particular method and apparatus for measurement of the refractive properties of the human eye as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for precompensating the refractive properties of an eye, the eye having, in order, a cornea, a pupil, a lens and a retina, said system comprising:

an optical means for generating a reflection from the retina of the eye;

a lenslet array for separating the reflection from the retina into a plurality of individual beams with each said individual beam having a unique optical path length;

a computer means for using said plurality of individual beams to create a digitized acuity map of the eye and to generate a signal, said digitized acuity map being indicative of the optical path lengths of said individual beams reflected from the retina, and said signal being indicative of a reverse of said acuity map; and an active mirror, said active mirror being programmed with said signal for precompensating light from a stimulus by reflecting the incoming light from said active mirror to make said optical path lengths of said individual beams appear to be substantially equal to each other.

2. A system as recited in claim 1 wherein said optical means further comprises:

a light source for directing a light beam through the cornea, through the pupil and through the lens, for reflection from the retina; and a variable aperture, said variable aperture being moveable between a first configuration wherein the light beam has a diameter of approximately 2 mm when entering through the pupil and a second configuration wherein the light beam has a diameter of approximately 6 mm when entering through the pupil, said first configuration being used to create a first acuity map and said second configuration being used to create a second acuity map.

3. A system as recited in claim 2 wherein said light beam is directed toward the eye as collimated light for subsequent focus by the cornea and the lens of the eye toward the retina.

4. A system as recited in claim 3 wherein said light beam has a wavelength equal to approximately seven hundred and eighty nanometers (780 nm).

5. A system as recited in claim 2 further comprising:

an optical means for sending a light beam for reflection from the apex of the cornea as a reflected light beam;

an illuminator for generating a pupil reflection from the eye; and a detector means for analyzing said pupil reflection for determining an "x-y" position for the eye, and for analyzing said reflection from the apex of the cornea for establishing a "z" position for the eye.

6. A system as recited in claim 2 further comprising:

an optical means for generating a reflection from the anterior surface of the cornea of the eye;

a lenslet array for separating the reflection from the cornea into a plurality of individual beams with each individual beam having a unique optical path length, said optical path lengths being used by said computer means to create a digitized topography map, said topography map being indicative of the optical path lengths of said individual beams reflected from the cornea; and a comparator means operable with said computer means for comparing said topography map of the cornea with said first acuity map and said second acuity map of the retina to enhance said signal.

7. A system as recited in claim 6 wherein said topography map is indicative of aberrations for the anterior surface of the cornea, wherein said first acuity map and said second acuity map are indicative of aberrations for the entire eye, and wherein said system further comprises a comparator means operable with said computer means to separate the aberrations of the anterior surface of the cornea and a predetermined aberration for the lens, from the aberrations of the entire eye to determine aberrations for the posterior surface of the cornea.

8. A system as recited in claim 7 wherein said aberrations of the posterior surface of the cornea are used by said computer means to model the posterior surface of the cornea.

9. A system as recited in claim 7 wherein the spherical aberration of the lens is determined with the lens in a relaxed state.

10. A system as recited in claim 7 wherein the predetermined aberration of the lens is determined by said computer means using a plurality of sequentially created said acuity maps.

11. A system as recited in claim 1 wherein a plurality of signals are collected to generate a time history of the refractive properties of the eye and said computer means uses said time history for diagnosing pathological problems of the eye.

12. A device for precompensating the refractive aberrations of an optical system which comprises:

means for directing a beam of monochromatic light through said optical system for reflection as a reflected light beam back through said optical system;

means for separating said reflected light beam into a plurality of individual beams;

means for determining a resultant refraction for each individual beam caused by the passage of said reflected light beam through said optical system;

means for compiling said plurality of resultant refractions to create a digitized acuity map of the refractive aberrations of said optical system;

means for inverting said digitized acuity map to create a reverse thereof;

means for generating a signal indicative of said reverse digitized acuity map; and means for programming an active mirror with said signal to create a reflective surface, said reflective surface being positioned to precompensate and direct incoming visible light toward said optical system.

13. A device as recited in claim 12 wherein said means for separating is a lenslet array and said means for determining includes an area sensitive detector.

14. A device as recited in claim 12 further comprising a computer wherein said computer includes said means for compiling, said means for inverting, said means for generating, and said means for programming.

15. A device as recited in claim 12 further comprising a variable aperture, said variable aperture being moveable between a first configuration wherein the beam of monochromatic light has a diameter of approximately 2 mm when entering said optical system and a second configuration wherein the beam of monochromatic light has a diameter of approximately 6 mm when entering said optical system, said first configuration being used to create a first said acuity map and said second configuration being used to create a second said acuity map.

16. A device as recited in claim 12 wherein said beam of monochromatic light has a wavelength equal to approximately seven hundred and eighty nanometers.

17. A method for precompensating the refractive aberrations of an optical system which comprises the steps of:

directing a beam of monochromatic light through said optical system for reflection as a reflected light beam back through said optical system;

separating said reflected light beam into a plurality of individual beams;

determining a resultant refraction for each individual beam caused by the passage of said reflected light beam through said optical system;

compiling said plurality of resultant refractions to create a digitized acuity map of the refractive aberrations of said optical system;

inverting said digitized acuity map to create a reverse thereof;

generating a signal indicative of said reverse digitized acuity map; and programming an active mirror with said signal to create a reflective surface, said reflective surface being positioned to precompensate and direct incoming visible light toward said optical system.

18. A method as recited in claim 17 wherein said optical system is an eye having, in order, a cornea, a pupil, a lens and a retina, and wherein said method further comprises the step of moving a variable aperture between a first configuration wherein the beam of monochromatic light has a diameter of approximately 2 mm when entering said optical system and a second configuration wherein the beam of monochromatic light has a diameter of approximately 6 mm when entering said optical system, said first configuration being used to create a first said acuity map and said second configuration being used to create a second said acuity map.

19. A method as recited in claim 18 further comprising the steps of:

generating a reflection from the anterior surface of the cornea of the eye;

separating the reflection from the cornea into a plurality of individual beams;

determining a resultant refraction for each individual beam caused by the reflection thereof from the anterior surface of the cornea;

compiling said plurality of resultant refractions to create a digitized topography map; and comparing said topography map with said first acuity map and said second acuity map to enhance said signal.

20. A method as recited in claim 19 wherein said topography map is indicative of refractive aberrations for the anterior surface of the cornea, wherein said first acuity map and said second acuity map are indicative of aberrations for the entire eye, and wherein said method further comprises the step of subtracting the aberrations of the anterior surface of the cornea, and a predetermined aberration for the lens, from the aberrations of the entire eye to determine aberrations for the posterior surface of the cornea.

21. A method as recited in claim 20 further comprising the steps of:

repetitively obtaining a plurality of enhanced said signals;

sequencing said plurality of enhanced said signals to prepare a time history of the refractive properties of the eye; and using said time history for diagnosing pathological problems of the eye.

* * * * *

UNITED STATES PATENT AND TRADEMARK OFFICE
CERTIFICATE OF CORRECTION

PATENT NO. : 6,155,684
DATED : December 5, 2000
INVENTOR(S) : Bille et al.

It is certified that error appears in the above-identified patent and that said Letters Patent is hereby corrected as shown below:

Column 7, Line 15
DELETE
[10]

Column 8, Line 19
DELETE
[12]

Signed and Sealed this

Fifteenth Day of May, 2001

Attest:

NICHOLAS P. GODICI

Attesting Officer    Acting Director of the United States Patent and Trademark Office